United States Patent [19]
Warrin et al.

[11] Patent Number: 5,125,837
[45] Date of Patent: Jun. 30, 1992

[54] APPARATUS AND METHOD FOR THERAPEUTIC LAVAGE AND SCALING OF TEETH

[75] Inventors: George E. Warrin, North Merrick; Rene J. Perdreaux, Brooklyn, both of N.Y.

[73] Assignee: Dentsply Management Corp., York, Pa.

[21] Appl. No.: 564,666

[22] Filed: Aug. 7, 1990

Related U.S. Application Data

[63] Continuation of Ser. No. 07/141,355, Jan. 6, 1988, abandoned.

[51] Int. Cl.⁵ .............................................. A61C 1/02
[52] U.S. Cl. ...................................... 433/98; 433/81; 433/86; 433/216
[58] Field of Search .................... 433/86, 81, 80, 98, 433/119, 216

[56] References Cited

U.S. PATENT DOCUMENTS

| | | | |
|---|---|---|---|
| 2,874,470 | 5/1954 | Richards | 433/85 |
| 3,077,415 | 6/1960 | Ayres | 106/75 |
| 3,091,033 | 5/1963 | Ellman | 433/86 |
| 3,213,537 | 10/1965 | Balamuth et al. | 433/98 |
| 3,368,280 | 2/1968 | Friedman et al. | 433/86 |
| 3,593,423 | 4/1969 | Jones et al. | 433/80 |
| 3,636,947 | 1/1972 | Balamuth | 128/66 |
| 3,645,255 | 2/1972 | Robinson | 433/119 |
| 3,693,613 | 9/1972 | Kelman | 128/24 A |
| 3,703,037 | 11/1972 | Robinson | 433/86 |
| 3,718,973 | 3/1973 | Slater et al. | 433/84 |
| 3,760,799 | 9/1973 | Crowson | 128/24 A |
| 3,807,048 | 4/1974 | Malmin | 433/81 |
| 3,809,977 | 5/1974 | Balamuth et al. | 128/24 AA |
| 3,863,628 | 2/1975 | Vit | 128/66 |
| 3,924,335 | 12/1975 | Balamuth et al. | 433/119 |
| 3,930,173 | 12/1975 | Banko | 310/26 |
| 3,956,826 | 5/1976 | Perdreaux, Jr. | 433/86 |
| 4,012,842 | 3/1977 | Vit | 433/216 |
| 4,116,239 | 9/1978 | Ewen | 128/200.16 |
| 4,148,309 | 4/1979 | Reibel | 128/24 A |
| 4,162,576 | 7/1979 | Takemoto et al. | 433/89 |
| 4,184,064 | 1/1980 | Williams | 433/27 |
| 4,247,288 | 1/1981 | Yoshii et al. | 433/81 |
| 4,249,901 | 2/1981 | Wieser | 433/119 |
| 4,260,380 | 4/1981 | Nash | 433/119 |
| 4,276,880 | 7/1981 | Malmin | 604/28 |
| 4,291,017 | 9/1981 | Beierle et al. | 424/52 |
| 4,295,827 | 10/1981 | Martin et al. | 433/81 |
| 4,330,278 | 5/1982 | Martin | 433/81 |
| 4,332,558 | 6/1982 | Lustig | 433/119 |
| 4,370,131 | 1/1983 | Banko | 433/86 |
| 4,428,748 | 1/1984 | Peyman et al. | 433/119 |
| 4,492,574 | 1/1985 | Warrin et al. | 433/81 |
| 4,505,676 | 3/1985 | Gonser | 433/119 |
| 4,592,728 | 6/1986 | Davis | 433/81 |
| 4,770,632 | 9/1988 | Ryder et al. | 433/80 |

FOREIGN PATENT DOCUMENTS

| | | |
|---|---|---|
| 0125784 | 11/1984 | European Pat. Off. ............ 433/119 |
| 446818 | 7/1927 | Fed. Rep. of Germany . |
| 180356 | 5/1954 | Fed. Rep. of Germany . |
| 7002091 | 5/1970 | Fed. Rep. of Germany . |
| 1469399 | 4/1977 | United Kingdom . |
| 8704613 | 8/1987 | World Int. Prop. O. . |

OTHER PUBLICATIONS

"Dentsply-Cavitron Powermatic Ultrasonic Dental Unit", Brochure, Dentsply International, 1976.

*Primary Examiner*—Gene Mancene
*Assistant Examiner*—Adriene B. Lepiane
*Attorney, Agent, or Firm*—Dale R. Lovercheck; Edward J. Hanson, Jr.

[57] ABSTRACT

An apparatus for scaling of teeth and lavage of the gingival sulcus is provided. The apparatus comprises a base unit which contains reservoirs for the medicaments used in the lavage procedure, and a handpiece connected to the base unit by a conduit, which contains an insert for scaling of teeth. Switches on the base unit and a footswitch make it possible for the practitioner to use the apparatus for scaling only, lavage only, or for simultaneous lavage and scaling.

22 Claims, 3 Drawing Sheets

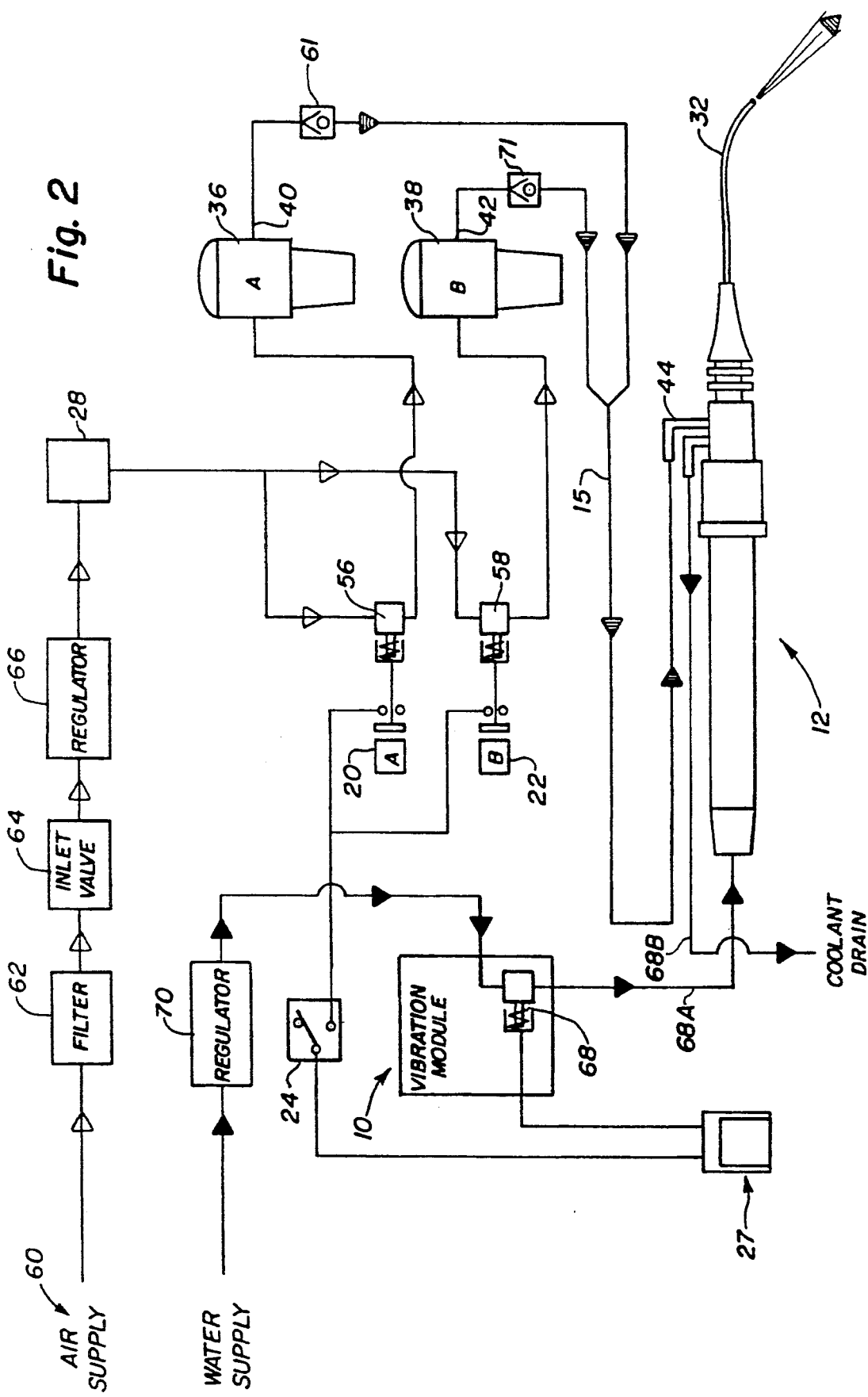

5,125,837

APPARATUS AND METHOD FOR THERAPEUTIC LAVAGE AND SCALING OF TEETH

This application is a continuation of application Ser. No. 07/141,355, filed on Jan. 6, 1988 and now abandoned Aug. 7,1990.

BACKGROUND OF THE INVENTION

The present invention relates to an apparatus for scaling of teeth, and for lavage of the gingival sulcus and other parts of the mouth requiring lavage. The apparatus is capable of providing scaling alone, lavage alone, or for providing both simultaneously.

It is known in the art that plaque and calculus harbor toxic and irritating components implicated in oral disease and that plaque and calculus can be removed from teeth by high frequency scaling. Many instruments are known in the art for that purpose. Prior art scaling instruments have been designed with scaling tips that are caused to vibrate at frequencies between about 6 and 50 KHZ using mechanical, magnetostrictive or piezoelectric energy. Scaling tips for the prior art devices are relatively large since they are used mainly to remove plaque and calculus from the exposed, relatively large, flat surfaces of teeth. With a few exceptions, prior art scaling tips are too large for scaling below the gum line in periodontal pockets, unless the pockets are surgically exposed.

Because heat is generated by the vibration of the stacks and scaling tips, most prior art scaling devices have a conduit that transports tap water to the handpiece and onto the scaling tip for cooling thereof. In magnetostrictive devices, for example, the tap water is first used to circulate around the transducer stack to cool the stack, and is then dispensed onto the scaling tip to cool the tip. In piezoelectric devices the cooling water is directed to the scaling tip only. The cooling water is thereafter dispensed into the patient's mouth during the scaling procedure to cleanse the operating field of debris.

It is also known in the art to provide instruments to oxygenate or irrigate periodontal pockets with oxygenated or oxygen producing chemicals. This is done because it has been found that anaerobic bacteria live in periodontal pockets, (it has been inferred that a causal relationship between the presence of anaerobic bacteria and periodontal disease exists) and anaerobic bacteria cannot live in the presence of oxygen. Similarly other antibacterial solutions may be prepared to facilitate removal of calculus, plaque and plaque components by irrigation. Such procedures are commonly known in the art as lavage.

It has been found that a conscientious program of keeping teeth clean of adhering calculus and plaque, and irrigating periodontal pockets with one or more suitable lavage irrigants may stop or even reverse the progression of periodontal disease.

In the past, however, to provide both procedures, two different apparatus were required. The practitioner, to provide adequate treatment, was faced with the expense and clutter of two independent sets of equipment, and the need to use both sets of equipment when using both procedures was time consuming and cumbersome.

It is the object of the present invention to overcome the problems with the prior art procedures and apparatus.

SUMMARY OF THE INVENTION

An apparatus for ultrasonic scaling of teeth and for therapeutic lavage is provided. The apparatus comprises a base unit having at least two fluid reservoirs having at least one outlet associated with each fluid reservoir; a handpiece comprising a handle connected to the base unit by at least one conduit, said conduit communicating with the outlets of the fluid reservoirs; and switching means for controlling dispensing of fluid from the reservoirs through the outlet to supply the handpiece with fluid from at least two reservoirs. The apparatus also has switching means for controlling an insert such that fluid may be dispensed through the insert without scaling or simultaneously with scaling.

Also provided is a method for prophylaxis or therapeutic treatment of teeth comprising simultaneously scaling teeth and lavage with a therapeutically effective medicament.

Also provided is an insert for scaling and lavage which has a unique shape which makes possible scaling below the gum line in a periodontal pocket and in other areas having limited accessibility.

BRIEF DESCRIPTION OF THE DRAWINGS

FIG. 2 is a schematic illustration of the apparatus of the invention.

FIG..5 is a cutaway view of a handpiece of the invention with a hollow tip and external flow return.

Figure 6:
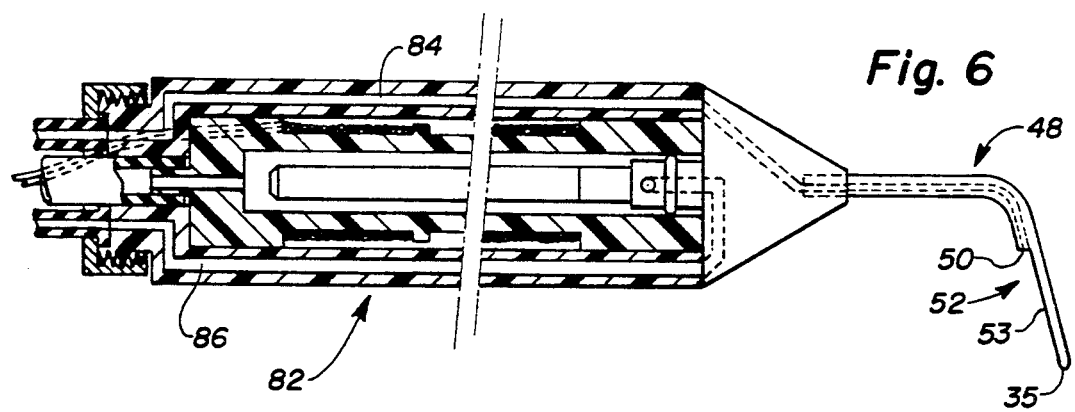

FIG. 6 is a alternative ultrasonic scaling, periodontal lavage insert.

Figure 7:
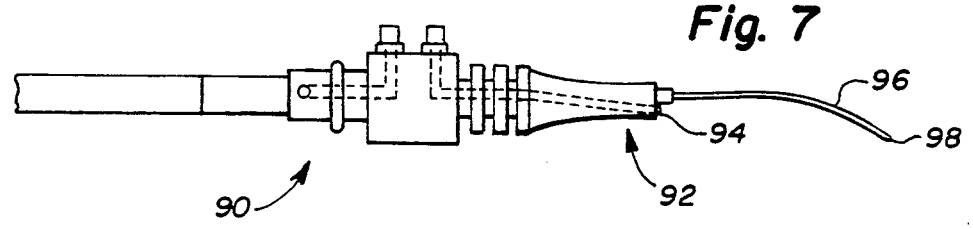

FIG. 7 is an alternative embodiment of a handpiece with means separate from the tip for spraying and cooling the tip.

DETAILED DESCRIPTION OF THE INVENTION

With reference now to FIGS. 1, 2, 3 and 5, the apparatus of the invention comprises a base unit 10, a handpiece 12 comprising handle 13 and insert 14 and foot switch 27. A conduit 15 connects the handpiece 12 to the base unit 10. Specifically, conduit 15 is connected to outlets 40 and 42 of separate cylindrical reservoirs 36 and 38, respectively, in base unit 10. Reservoirs 36 and 38 are provided to store one or more medicament fluids that can be transported from the reservoirs to be dispensed through handpiece 12 and insert 14 when desired. Fluid can be introduced into reservoirs 36 and 38 through a refill opening therein which are closed by caps 16 and 18 respectively.

In the illustrated embodiment, handle 13 has means therein which is adapted to impart a vibration to insert 14. Such means are well known in the art and may be mechanical, magnetostrictive or piezoelectric in nature. As is known in the art, when the tip 32 of insert 14 is touched lightly against a tooth by the practitioner, tip 32 is capable, because of its vibratory movement, of removing plaque and calculus from the tooth.

As is known to those skilled in the art, scaling tips adapted to vibrate anywhere from 6 to 50 KHZ may be used for scaling of teeth. In the illustrated embodiment, power control 26 may be used to vary the power of handle 13. Frequencies above about 20 KHZ are generally considered to be in the ultrasonic range.

The apparatus of the invention may be used as a conventional ultrasonic scaler, in which case switch 24 will be set to a first setting (condition 1). In condition 1, stack cooling water is used to cool the scaling tip and to irrigate the mouth during ultrasonic scaling. The medicament delivery system from reservoirs 36 and 38 to the scaler tip is not activated. In condition 1, activation of the ultrasonic scaler is controlled by foot control 27. The foot control has two positions. Depressing the foot control to either position will result in activation of the ultrasonic handpiece and delivery of the stack cooling water to the insert tip 32. When the foot is removed from the foot control 27, both the ultrasonic handpiece and water are shut off.

Conventional ultrasonic inserts of the magnetostrictive type have a flow through passage that utilize the water used to cool the transducer stack to also cool the scaling tip. The flow of the cooling water is conventionally set at about 35 cc/min and can be further controlled using flow control knob 25. When foot control 27 is depressed, solenoid valve 68 is activated permitting the flow of water through regulator 70, through solenoid 68 and conduit 68A to handpiece 12 and over the scaling tip; vibration of insert 14 is also initiated. Insert 12 is connected through conduit 68B to a coolant drain.

The apparatus of the invention may also be used for simultaneous ultrasonic scaling and delivery of medicaments to the scaling tip. For the simultaneous function, switch 24 will be set to a second setting (condition 2). In condition 2, activation of the ultrasonic scaler and the medicament delivery system is controlled by foot control 27. The foot control has two positions. Depressing the foot control to the first position will result in the handpiece only delivering medicament to the tip of the insert. The particular medicament to be delivered from reservoir 36 and/or 38 is controlled by buttons 20 and 22, respectively. Depressing the foot control to the second position will result in activation of the ultrasonic handpiece and delivery of medicament to the tip of the insert. In condition 2, stack cooling water is used only to cool the transducer stack. When the foot is removed from foot control 27, all functions to the handpiece are shut off.

More specifically when switch 24 is set to a second setting (condition 2) the apparatus is adapted for lavage by activating solenoids 56 and 58 which are put into operation by depressing one or both of buttons 20 and 22 and depressing foot control 27 to its first position. When the apparatus is in this condition, air pressure from air supply 60 is reduced by regulator 66 forcing fluid from either reservoir 36 or 38 or both into conduit 15, through inlet 44 to insert 14 and through scaling tip 32 to be dispensed in the mouth. In the preferred embodiment the air pressure will be controlled by regulator 66, and the air supply will be maintained adjustably by control knob 28 at about 2-16 psi.

As is conventional in the art, the air supply line will be equipped with at least one filter 62, an inlet solenoid valve 64 and a regulator 66.

Those skilled in the art will recognize that in an alternative embodiment reservoirs 36 and 38, or the lines leading therefrom can be equipped with pump means for dispensing fluid from reservoirs 36 and 38.

It is also preferred that the lines leading from reservoirs 36 and 38 be equipped with check valves 61 and 71 which are used to insure that flow in the line is only in one direction. This prevents, for example, the flow of fluid from reservoir 38 to reservoir 36 when dispensing fluid from only reservoir 38. Vibration in insert 14 is initiated when footswitch 27 is pushed to its second position By, controlling the air pressure in the line as described above, flow control 28 is used to control the flow rate of fluid from reservoirs 36 and 38.

Circuitry may be provided which prevents activation of the vibration in the handpiece unless one or both of buttons 20 and 22 are depressed. This ensures that cooling fluid will always be available to tip 32 when insert 14 is vibrating.

In a preferred embodiment, especially for treating patients with gingivitis and periodontal disease, the practitioner may depress button 20, which will deliver a particular medicament to the handpiece from reservoir 36 through outlet 40; or he may depress button 22, which will deliver another medicament from reservoir 38 through outlet 42; or he may depress both buttons 20 and 22 to deliver a predetermined ratio of the medicaments from reservoirs 36 and 38 to handpiece 12.

In a preferred embodiment employing a handpiece using magnetostrictive elements, outlets 40 and 42 will connect within base unit 10 so that only one tube is needed to connect base unit 10 to handpiece 12 through inlet 44. Those skilled in the art, however, will recognize that, for some applications it may be more suitable to employ two or more conduits to connect base unit 10 to handpiece 12 so that the fluids from reservoirs 36 and 38 will combine in the handpiece, just before they are dispensed through insert 14. Using such an arrangement reduces the amount of flush time needed to clean the line when switching from one fluid reservoir to another. Besides the tube for medicaments connecting base unit 10 to handpiece 12, conduit 15 may contain one tube to carry cooling water to the transducer stack 30 and one tube to return cooling water from the handpiece 12 through outlet 46 to a sink or other depository, and the electrical wires needed to control the handpiece.

In an alternative embodiment, those skilled in the art will recognize that measured amounts of lavage irrigants, especially disinfecting fluids, may be used to first cool a transducer stack and be delivered through insert 14 to the area of operation.

As used herein, the term medicament includes antibacterial solutions adapted to fight bacteria associated with periodontal disease or dental caries, solutions adapted to increase resistance to dental caries such as fluoride solutions, surfactants adapted to chemically clean the sulcus and teeth of calculus and plaque and endotoxins, as well as chemical solutions containing chemicals to promote healing.

In the preferred embodiment scaler tip 32 will be made of stainless steel, will be tapered and will have dimensions suitable for entry into a periodontal pocket and will have roughly the dimensions of a periodontal probe. In the illustrated embodiment scaler tip 32 at end 37 is about 0.6 mm in diameter with a concentric oral delivery orifice 34 of about 0.25 mm in diameter. Those skilled in the art will recognize that if stronger and tougher alloys are used for making scaler tip 32, that a tip with smaller dimensions, if desired, can be made.

The amplitude of the insert 14 in ultrasonic operation will depend on the particular geometry of the particular insert used as well as the power output of the handpiece. The stroke amplitude can be therefore controlled by power control 26 to maintain clinical effectiveness and increase patient comfort when used subgingivally.

Figure 1:
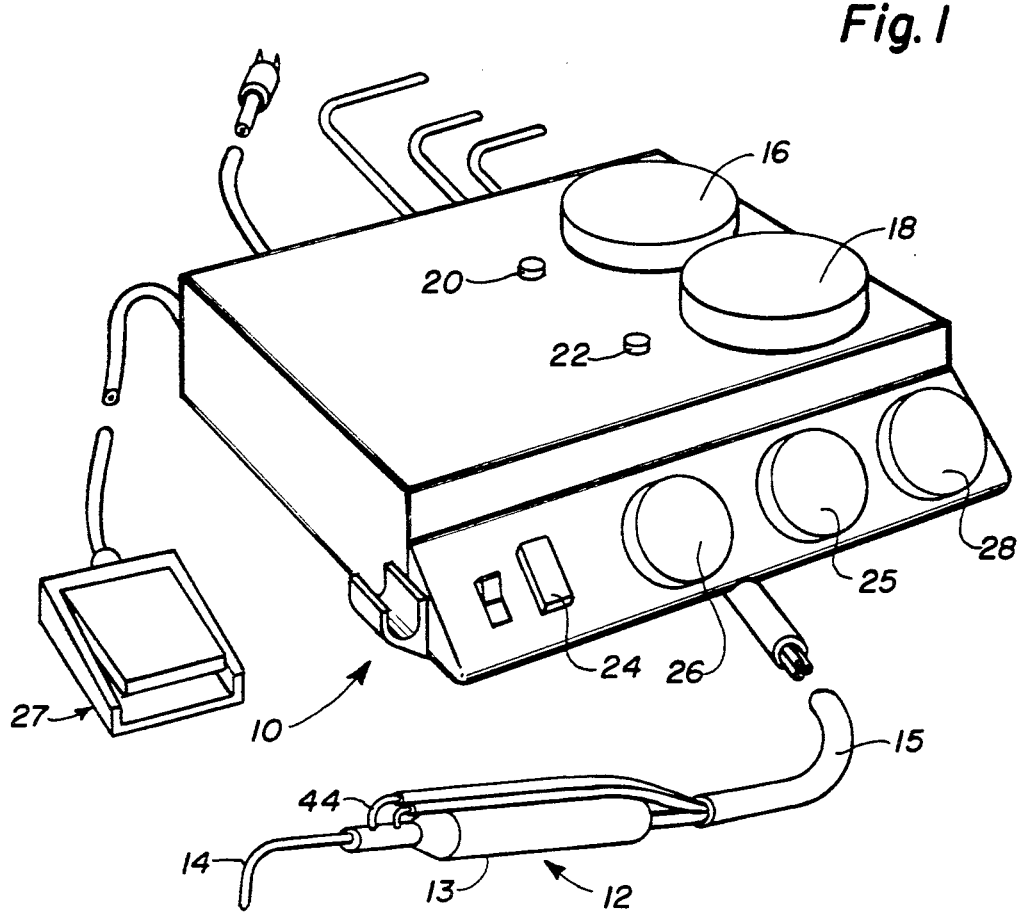
FIG. 1 is a perspective view of the apparatus of the invention including the base unit, foot switch and handpiece.
Figure 3:
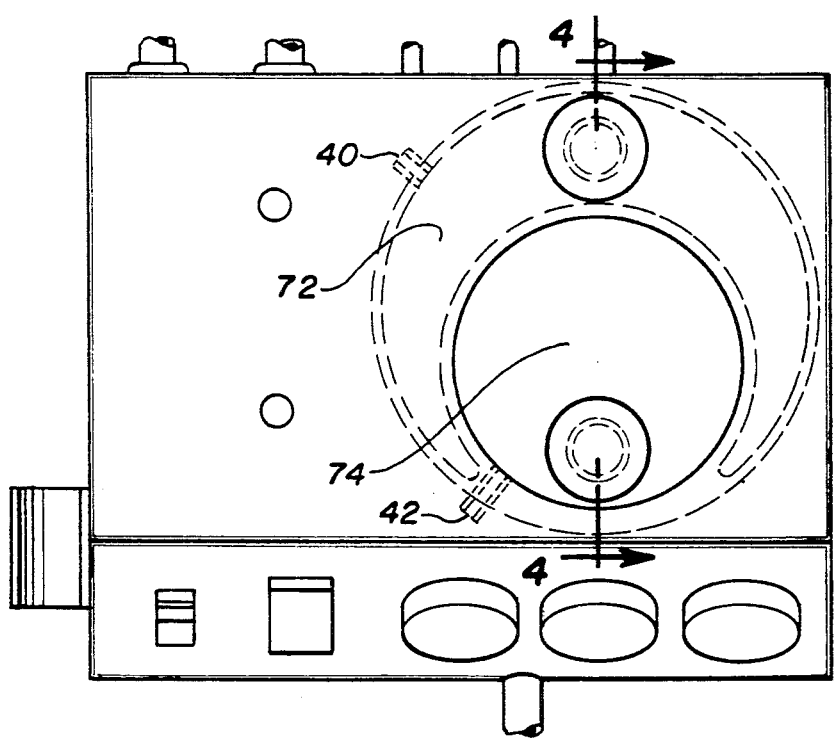
FIG. 3 is a cutaway top view of the base unit of the invention illustrating an alternative embodiment of the reservoir configuration.
Figure 4:
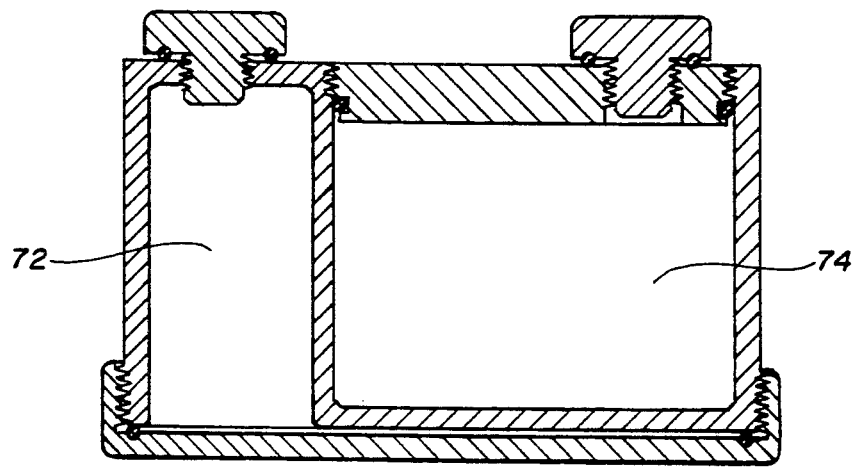
FIG. 4 is a cutaway side view along line 4—4 illustrating an alternative embodiment of the reservoir configuration of FIG. 3.

With reference now to FIGS. 3 and 4, in an alternative embodiment of base unit 10, reservoirs 72 and 74 may be contained within a single cylinder where reservoir 72 surrounds reservoir 74. Such a configuration utilizes available space efficiently and such a configuration may be desirable in an embodiment where larger reservoirs, in the order of 1000 ml, are used.

Figure 5:
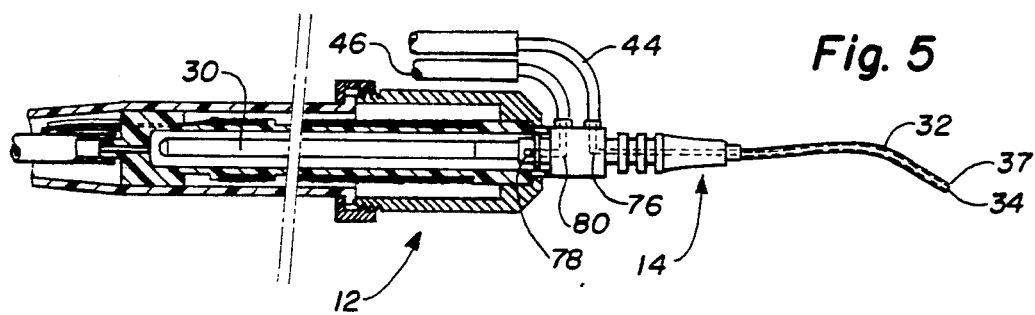

With reference now to FIG. 5 in the preferred embodiment, irrigant will be delivered through the scaler, tip 32 through orifice 34 in apex or end 37 of scaler, tip 32. Handpiece 12, having an insert 14, has an insert tip 32 with dimensions suitable for use in a periodontal pocket when the apparatus is operated in condition 2. Irrigant, preferably a medicament from reservoir 36 or 38, or both, enters insert 14 through inlet tube 44, travels through passage 76 and is dispensed through orifice 34. Hole 78 in insert 14 permits cooling water that passes over stack 30 to enter passage 80 to be conveyed through outlet 46 to be dispensed in the sink or other depository. An insert tip 32 with an apical orifice 34 is particularly suited for lavage of a periodontal pocket. When irrigant is dispensed from tip 32 while it is vibrating, the irrigant is dispensed in a fine spray which helps clear the working area of debris. When used subgingivally in a periodontal pocket, this embodiment assures good irrigation of the pocket and debridment of plaque and calculus.

With reference now to FIG. 6, an alternative handpiece 82 having an irrigant delivery tube 84 and a flow return tube 86 contained within the handpiece is illustrated. Handpiece 82 operates in the same manner as described for handpiece 12 in FIG. 5, but does not have the extraneous external tubing. Insert tip 48 is designed having a spray outlet 50 above the apex 35 and cutaway side 52 providing an external channel 53 on insert tip 48. Such an insert may be used to provide, for some applications, an alternative spray geometry in the treatment.

It will be recognized by those skilled in the art that an insert having a cutaway insert tip 48 may be used as part of a handpiece 12 and an insert tip 32 may be used as part of a handpiece 82, as FIGS. 5 and 6 are illustrative only and are not limiting.

With reference now to FIG. 7, in another alternative embodiment, insert 90 may have an end 92 having an outlet 94 for dispensing cooling or medicament fluid on to insert tip 96 which has an external channel for directing the fluid to apex 98 of the tip. In this embodiment, since the cooling fluid is external to tip 96, tip 96 may be made of a solid piece of metal. Such an embodiment permits further reduction in the size of the tip and may provide a longer lasting tip.

In the preferred embodiment scaler tip 32 will have an angle of about 105°–140° preferably 135° in reference to the stack axis and will be about 11–21 mm long preferably about 19 mm long.

Those skilled in the art will recognize that a functional tip may be provided having different lengths and different working angles.

Those skilled in the art will recognize that all connectors and tubing used in the base unit, the conduit and the handpiece will be inert to the medicaments and irrigants used in the apparatus. In the preferred embodiment, the tubing and all connectors will be molded or extruded thermoplastic.

In a preferred embodiment, tip 32 will be brazed to stack 30 of insert 14.

In an attenuator embodiment a tip may be provided which can be connected to the insert by a collet. In such an embodiment the tip may be designed to be disposable.

The medicaments dispensed from reservoirs 36 and 38 may be chosen to specifically effect a particular treatment. For example, hydrogen peroxide or a chlorohexidine solution may be chosen for the treatment of periodontal disease; zinc chloride solution, cetylpyridinium chloride solution, or a stannous fluoride solution may be chosen to treat plaque, or for treatment of dental caries, or a surfactant solution may be used for chemically removing endotoxins from the surface of the teeth and gums. Since buttons 20 and 22 may be depressed to permit flow from reservoirs 36 and 38 to occur simultaneously, the practitioner has the capability of providing treatment for periodontal disease and plaque simultaneously. As is known to those skilled in the art, some of the medicaments which are desirable for use in such treatments are short-lived and cannot be stored in a condition ready for use. Accordingly, using reservoirs 36 and 38 to store the components of short-lived medicaments makes it possible to form the desired medicaments in situ by delivering the two components from reservoirs 36 and 38 simultaneously to form the desired, short-lived medicament in the mouth or the handpiece or the conduit leading to the handpiece.

The medicaments distributed from reservoirs 36 and 38 may be any of those known to those skilled in the art to be effective in the treatment of periodontal disease. In the preferred embodiment the irrigants will be selected from the group comprising solutions containing hydrogen peroxide, zinc chloride with or without sodium fluoride, quaternary compounds including cetylpyridinium chloride, stannous fluoride, chlorine dioxide, sodium bicarbonate, chlorohexidine (for example chlorohexidine gluconate) and mixtures thereof.

Irrigant is dispensed through the scaler tip 32 or 48 in sufficient volume to remain constantly available to infected sites. The flow rate desired will depend on the patient and the particular treatment desired. The flow rate of irrigant will be about 3–20 ml/min and most preferably 5–10 ml/min. The flow rate for a particular treatment may be controlled by flow rate control knob 28. The capacity of reservoirs 36 and 38 will be such that irrigant storage is sufficient for about 5 minutes to 5 hours, and preferably at least 10–20 minutes of continuous use. Accordingly, the capacity of each reservoir may be from about 100 to 1000 ml and more as desired.

In its operation, when switch 24 is in the condition 2 position, the apparatus will be adapted for scaling while dispensing medicament from one or both of reservoirs 36 and 38. When button 22 is depressed, medicament will be distributed from reservoir 38 through outlet 42 and into conduit 15. The medicament will flow through conduit 15 to handpiece 12, through inlet 44 to insert 14. The medicament will flow through insert tip 32 and will be dispersed through orifice 34 at the end 37 of tip 32. Tip 32 has a shape and size, and has a tapered end 37 at orifice 34 such that it will fit into a periodontal pocket. End 37 has a shape and strength suitable for scaling of teeth.

Optionally, for the comfort of the patient, the apparatus may be provided with a small heater in hand-piece 12 or in conduit 15 to aid in heating the irrigant dispensed in the mouth to about 35°-38° C.

Since its flow through the apparatus and its flow through the scaling tip may cause medicament solutions to foam, as will be appreciated by those skilled in the art, it may be desirable to add antifoaming agents to the medicament solution to reduce the foaming.

For the convenience and comfort of the patient, it is desirable to add a flavor to the medicament solution.

In the preferred embodiment of the invention, the medicament fluid used as an irrigant will have antibacterial activity sufficient to substantially destroy airborne bacteria in the operatory.

Examples of medicament compositions that may be used as irrigants for scaling and periodontal lavage are illustrated in, for example, U.S. Patents

| | |
| --- | --- |
| 3,864,472 | 4,472,373 |
| 3,887,701 | 4,522,806 |
| 4,160,821 | 4,582,702 |
| 4,339,432 | 4,601,900 |

Those skilled in the art will be able to determine which compositions described therein will most beneficially be used in the apparatus of the invention.

Illustrated embodiments of fluid solutions that may be used in the apparatus of the invention follow.

In the following examples:

Hystar 5875 is hydrogenated starch hydrolysate available from LONZA,

Flavor is a spearmint oil/peppermint oil flavor available from Unter & Co.

SDA-38B, SDA-37B and SDA-36B are 200 proof alcohol.

EXAMPLE 1

| INGREDIENTS | PERCENT |
| --- | --- |
| Water Purified | 85.3275 |
| Hystar 5875 | 2.0000 |
| Sodium Saccharin | 0.0500 |
| Sodium Citrate | 0.1000 |
| Zinc Chloride | 0.1500 |
| Sodium Fluoride | 0.0200 |
| FD & C Green #3 | 0.0005 |
| FD & C Yellow #10 | 0.0020 |
| Tween 80 | 0.5000 |
| Flavor | 0.2500 |
| SDA-37B, ethanol | 11.6000 |
| | 100.0000 |

EXAMPLE 2

| INGREDIENTS: | PERCENT: |
| --- | --- |
| Water Purified | 84.09425 |
| Hystar 5875 | 2.00000 |
| Spectradyne G (20% chlorohexidine solution) | 0.80000 |
| Sodium Saccharin | 0.00500 |
| D & C Yellow #10 | 0.00025 |
| D & C Yellow #6 | 0.00050 |
| Tween 80 | 1.0000 |
| Flavor | 0.5000 |
| SDA-38B, ethanol | 11.6000 |
| | 100.0000 |

EXAMPLE 3

| INGREDIENTS: | PERCENT: |
| --- | --- |
| Water Purified | 77.45465 |
| Hystar 5875 | 2.00000 |
| Sodium Saccharin | 0.05000 |
| Benzoic Acid | 0.00010 |
| Cetylpyridinium Chloride | 0.04500 |
| FD & C Blue #1 | 0.00025 |
| Tween 80 | 1.0000 |
| Flavor | 0.5000 |
| SDA-36B, ethanol | 18.9500 |
| | 100.0000 |

While present embodiments of the invention and methods of practicing the same have been illustrated and described, it will be recognized by those skilled in the art that this invention may be otherwise variously embodied and practiced within the scope of the following claims.

What is claimed is:

1. An apparatus for scaling of teeth and for therapeutic lavage comprising:
   (a) a base unit having at least two fluid reservoirs each of said reservoirs having an outlet;
   (b) a handpiece having a handle and an insert, said insert having tooth scaling means, said insert being connected to said outlet by a first conduit means, said first conduit means communicating with said outlets of said fluid reservoirs to supply fluid from said fluid reservoirs to the subgingival area of treatment;
   (c) a first switching means for controlling dispensing of medicament containing fluid from said reservoirs through said first conduit means to said handpiece;
   and
   (d) a second switching means for controlling cooling fluid passage through a second conduit means connected to said handpiece to provide cooling fluid through said insert, whereby medicament containing fluid may be dispersed through said insert without scaling or simultaneously with scaling.

2. The apparatus of claim 1 in which said handpiece has means for producing ultrasonic vibrations in said insert when said insert is a transducer.

3. The apparatus of claim 2 in which said means for producing ultrasonic vibrations comprises a coil which produces an alternating magnetic field in said handpiece.

4. The apparatus of claim 2 in which said ultrasonic vibration causes heating of fluid in said handpiece.

5. The apparatus of claim 1 in which air pressure is used to provide flow of fluid from said fluid reservoirs to said handpiece.

6. The apparatus of claim 1 in which said base unit has pump means for activating flow of fluid from said fluid reservoirs to said handpiece.

7. The apparatus of claim 1 in which said insert for scaling of teeth has means by which medicament is dispensed through said insert during scaling to simultaneously deliver irrigants to the sulcus and clear the pocket of debris and chemomechanically clear the sulcus of infection.

8. The apparatus of claim 1 in which said insert has a tapered tip which is dimensioned to fit into a periodontal pocket and in which fluid from at least one of said reservoirs is dispensed through said handpiece when said insert is used without vibration to deliver said fluid directly to a pocket bottom.

9. The apparatus of claim 8 in which said insert has an external channel for delivery of the fluid from the handpiece to said periodontal pocket on the outside of said tip.

10. The apparatus of claim 1 in which said insert has a tip about 11 to about 21 mm long, said tip being at an angle of between about 105°–140° with respect to the handpiece axis.

11. The apparatus of claim 1 in which a compound bend exists to provide a larger contact surface with the tooth.

12. The apparatus of claim 1 in which said insert has a tip about 19 mm long, said tip being at an angle of about 135° with respect to the handpiece axis.

13. The apparatus of claim 1 wherein said fluid reservoirs and said handpiece and inserts are adapted to hold and dispense fluid selected from the group consisting of solutions of hydrogen peroxide, stannous fluoride, chlorine dioxide, sodium bicarbonate, zinc chloride, quaternary ammonium compounds including cetylpyridinium chloride, chlorohexidine, water and mixtures thereof.

14. The apparatus of claim 1 in which an internal return is provided for coolant which is used to cool said insert.

15. The apparatus of claim 1 in which said at least two fluid reservoirs are concentrically arranged within one cylindrical configuration.

16. An apparatus for therapeutic lavage and scaling of teeth comprising:
   a reservoir,
   a base unit,
   a handpiece,
   a first switching means for controlling dispensing of medicament containing fluid,
   a medicament conduit, and
   a second switching means for controlling water passage from a water supply,
   said reservoir being supported by said base unit, said handpiece having a handle and an insert, said insert having tooth scaling means, said first switching means being connected to said reservoir, said reservoir being connected to said medicament conduit, said medicament conduit being connected to said insert, said handpiece being connected to said second switching means, whereby medicament containing fluid is readily applied from said reservoir to a subgingival area of treatment through said insert, and water is readily passed to said handpiece.

17. The apparatus of claim 16 further comprising an air supply, said air supply being connected to said first switching means said first switching means being adapted to control passage of medicament containing fluid through said insert.

18. The apparatus of claim 16 further comprising a water supply, said water supply being connected to said second switching means, whereby said second switching means is adapted to control water passage through said insert.

19. The apparatus of claim 16 wherein said apparatus comprises at least two reservoirs each connected to said medicament conduit.

20. The apparatus of claim 16 wherein said tooth scaling means is an ultrasonic scaling means.

21. The apparatus of claim 16 wherein said has a tip and has an external channel and a dispensing port opening into said channel.

22. A method for therapeutic lavage and scaling of teeth comprising:
   providing a reservoir, a base unit, medicament conduit, a handpiece, a first switching means for controlling dispensing of medicament containing fluid, a second switching means for controlling water passage from a water source, said handpiece having a handle and an insert, said insert having tooth scaling means, said reservoir being supported by said base unit, said first switching means being connected to said reservoir, said reservoir being connected to said medicament conduit; said medicament conduit being connected to said insert, said handpiece being connected to said second switching means,
   applying medicament containing fluid from said reservoir through said insert to a subgingival area of treatment, and
   conveying cooling water from said water source through said insert.

* * * * *